US00RE41319E

(19) United States
(12) Reissued Patent
Bradley et al.

(10) Patent Number: US RE41,319 E
(45) Date of Reissued Patent: May 11, 2010

(54) PORTABLE CONTAMINANT SAMPLING SYSTEM

(76) Inventors: Bruce J. Bradley, 160 Bridon Way, Jerome, ID (US) 83338; Dirk V. Clarksen, P.O. Box 693, Jerome, ID (US) 83338

(21) Appl. No.: 11/955,183

(22) Filed: Dec. 12, 2007

Related U.S. Patent Documents

Reissue of:
(64) Patent No.: 7,100,461
Issued: Sep. 5, 2006
Appl. No.: 10/376,572
Filed: Feb. 27, 2003
(60) Provisional application No. 60/360,400, filed on Feb. 27, 2002.

(51) Int. Cl.
*G01N 1/00* (2006.01)

(52) U.S. Cl. ..... 73/864.33
(58) Field of Classification Search ..... 73/863.23, 73/864.33, 864.34, 864.73, 864.71
See application file for complete search history.

(56) References Cited

U.S. PATENT DOCUMENTS 3,362,141 A 1/1968 Royster et al.
3,748,905 A 7/1973 Fletcher et al.
3,977,254 A 8/1976 Brouwer
4,092,845 A 6/1978 Prodi et al.
4,208,912 A 6/1980 Baldeck
4,363,639 A 12/1982 Gladon
4,936,878 A 6/1990 Gustavsson et al.
5,109,849 A 5/1992 Goodman et al.
5,253,538 A 10/1993 Swick et al.
5,463,909 A 11/1995 Eldridge
5,783,938 A 7/1998 Munson et al.
5,939,647 A 8/1999 Chinn et al.
6,338,282 B1 1/2002 Gilbert
6,408,701 B1 6/2002 Fujita
6,453,759 B1 9/2002 Lebski et al.

*Primary Examiner*—Robert R Raevis
(74) *Attorney, Agent, or Firm*—Robert L. Shaver; Dykas, Shaver & Nipper, LLP

(57) ABSTRACT

The invention is a portable sampling system for sampling various media for contaminants. The media sample can include gases, liquids, and dry powders. The contaminant sample can include gaseous components, particulates of various kinds, and microorganisms. The system can be used to sample the surfaces of fruits and vegetables, meat carcasses, the interior of envelopes of other containers, gases in rooms or containers, and surfaces such as countertops, a vehicle exterior, skin, and clothing.

8 Claims, 11 Drawing Sheets

20
22
23
16
44

PORTABLE CONTAMINANT SAMPLING SYSTEM

Matter enclosed in heavy brackets [ ] appears in the original patent but forms no part of this reissue specification; matter printed in italics indicates the additions made by reissue.

PRIORITY

This application claims priority from the provisional application filed on Feb. 27, 2002 with application Ser. No. 60/360,400 entitled Wet Vacuum Sampler For Surface Biocontamination Detection.

BACKGROUND OF THE INVENTION

1. Field of the Invention

The present invention generally relates to environmental samplers, and more particularly relates to portable field samplers for microorganisms, particulate contaminates, and gasses.

2. Background Information

There are a number of situations in which it is desirable to take samples in the field of various contaminants of interest. Such samples could be taken of gases in a room or a tank. Samples could also be taken of liquids in a container or on a surface. Samples may also be taken on the surface of an object, such as a countertop, a particular food object such as an apple, or the surface of a machine or tool. At present, gas is sampled through the use of a portable test unit that uses a bulb and valves to draw air into chambers for testing. Such devices are used to test exhaust gases of boilers, for instance to test for oxygen content, carbon monoxide, and other gases. The prior art method of sampling surfaces is practiced on such diverse applications as meat carcasses in the food industry, and on the exterior surface of the NASA spacecraft as part of NASA's Planetary Protection Program.

In the case of meat carcasses, the surfaces of the carcasses are tested by a method that is aimed at standardizing a surface testing method. The method is to place a template over a section of meat carcass and then use a sponge to wipe the exposed carcass inside of the template. The wiping pattern is specified and the thought is to use a standardized swabbing method to obtain results that can be compared from one carcass to another. The problem with this is that at the microscopic level, a meat carcass is extremely rough and has cracks and crevices that are untouched by the sponge of the swab. For this reason, the swab passing over the tops of these cracks yields a very inaccurate count of the bacteria that may be present on the meat carcass.

A similar swabbing technique is also used for testing the surface of a spacecraft for exobiological contamination. However, even stainless steel has porosities in which bacteria sized organisms can lodge and be safe from a swab passing over that surface. Similarly, Formica, plastics, ceramic tile, grout, rubber, and almost anything conceivable that has grooves, cracks, and crevices at the microscopic level that makes a surface swab ineffective.

The practice of sampling for the food industry is discussed further below, but it is to be understood that the same principles apply to any type of surface sampling situation, whether sampling for radioactive particles or bacteria.

Although food borne illness is declining in some areas of the world, billions of dollars and thousands of lives are still lost annually due to food borne pathogens. Rapid bacterial detection techniques are limited in the real world by inadequate sample acquisition. Improved sampling methods are needed throughout the food industry from farm to table in order to better protect the public well-being.

Current non-destructive meat carcass sampling methods available to the industry collect bacteria located on or very near the surface. These microbes on the top surface represent only a portion of the bacteria present on meat carcass surfaces as demonstrated by significantly increased bacterial recovery using the present invention of sample collection immediately following sponge or swab sampling. Similar circumstances likely apply to macro or microscopically porous food preparation surfaces, such as cutting boards, conveyor belts, and some grinding or processing bins and equipment. In addition, cross-contamination between multiple sampling areas may be significant with sponge sampling. Minute hydrophobic surface cracks and crevices on carcasses may provide adequate protection for microbes to escape during surface anti-microbial solution treatments and during collection with sponge or swab surface sampling procedures.

An object of the present invention is to provide a sampling means comparable to the excision method, but that does not destroy the sampling surface. The microbial collection and concentration device of the present invention meets these needs.

In addition, the present invention has been developed with a focus on improved food safety through better sample collection from meat carcasses, and from food preparation surfaces and containers.

Another object of the present invention is to provide a collection/capturing means that can non-destructively sample/collect bacteria from items such as meat carcass in a more proficient means, especially out of surface cracks and indentations.

Another object of the present invention is to provide an application that can be utilized by a single person and thus reduce labor costs.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

These and other objects are accomplished by the portable containment sampling system of the present invention. This takes the form of a portable system whose components are contained in a box like frame called a support equipment pack. The support equipment pack can include a lid on hinges, and is meant to be self-contained and transportable to field operations. It can be powered by onboard batteries, or it can use 110 volt current, which may be supplied from a building outlet, from a 110 volt outlet powered by a vehicle using an inverter, or a power generator.

The portable contamination sampling system includes an air pump, whose purpose is to draw a sample into a collection unit. A variety of contaminants may be sampled from a number of different matrices. For instance, dry powders may be drawn into the collection unit when sampling envelopes for anthrax spores. Similarly, dry surfaces can be sampled for particles such as radioactive particles, chemical warfare agents, or other dry particles. Air may also be sampled, such as air in a clean room, gases in exhaust stacks, or gases in open or closed environments. Surfaces may also be sampled using a spray of rinse solution, which is sprayed out and drawn back into the collection unit by the air pump.

The collection unit can take a number of configurations, but it is an essential feature of the collection unit is that it is designed to collect a contaminant of interest in a chamber that may be hermetically sealed. The collection unit is designed to be removed from the portable contamination sampling system so that it can be sent to a lab for further analysis. The collection unit is also configured for contaminant detection of enclosed contaminants, be they microbes, gases or particles. The collection unit is also suitable for storing these contaminants, and may be used to hold the contaminants for analysis at a later date.

The system also includes a handheld sampling tool. The sampling tool is connected to the air pump via the collecting unit and tubing. It is configured for drawing in a sample in a gas or liquid matrix and transporting the sample to the collection unit where it is filtered and held for later activities. The handheld sampling tool can take a number of different configurations as discussed below.

The sampling tool is connected to the collection unit by a sample tool tube, which is typically a section of tygon or other flexible tubing.

A second embodiment of the sampling unit includes a collection unit that is configured with a hydrophobic filter. The hydrophobic filter provides a positive seal to the collection unit so that liquids that enter the collection unit cannot leave the collection unit, and thus contaminants of interest stay within the liquid or media in the collection unit for later analysis. The hydrophobic filter is positioned operatively between the input opening of the collection unit and the air pump. This means that the hydrophobic filter may be positioned adjacent the output opening of the collection unit, or even as an inline filter in the tubing that goes from the collection unit to the air pump. However, it is preferably placed in a position inside the collection unit that blocks the liquids in the collection unit from entering the output opening.

The hydrophobic filter described above would typically be a fibrous material that is coated with hydrophobic material to form a fibrous material that has hydrophobic properties. Such hydrophobic filters are commonly made of Teflon, polytetrafluoroethylene (PTFE), or PTFE coated fibrous filters, or other type of filters. Obviously, other hydrophobic materials would be suited for use in this filter application, including non-fibrous membranes or barriers made of hydrophobic material such as Gortex or similar materials.

Either of the above described collection units may be configured to sample gas. In the gas sampling configuration, a catchment liquid is placed in the collection unit, and a gas sample is passed through the catchment liquid by a tube that impinges gas into the catchment liquid. This configuration of collection unit may be utilized to test gases, or particles that are suspended in gases. The catchment liquid may be chosen to absorb a particular gas or to capture a particle that is entrained within the gas sample matrix.

The collection unit configured for sampling gases may include an elongated tube that extends into the catchment liquid, through which a gaseous sample matrix is impinged into the catchment liquid for capture of the contaminant of interest. This version of the device may include one or more baffle disks that are mounted to the elongated tube. The baffle disk is configured to block the discharge of catchment liquid from bursting bubbles. Bursting bubbles tend to eject a droplet of liquid when they burst. Such drops of liquid can lodge on the upper side walls of the collection unit and dry there. This is undesirable because if there are microbes in the droplets, they can be injured by desiccation on the side wall of the collection unit. The baffle disks block such a discharge of droplets from bursting bubbles. The baffle disk may also be configured to move up and down the elongated tube on which it is centered. The baffle disk may be configured to be light enough to be lifted up by the bubbles under it to periodically rise up the elongated tube and basically rinse of the inner walls of the collection unit. A baffle disk that is in a generally frustoconical or generally conical shape has been found to perform this function well. It is periodically lifted by the collection of foam and bubbles to the upper regions of the collection unit and rinses the walls of the dried catchment liquid and contaminants.

Another configuration of the collection unit is designed to receive liquid from the sampling surface that has been sprayed onto the sampling surface to dislodge contaminants of interest, be they microbes or dry particles. In this configuration of the device, the portable contaminant sampling system includes a rinse solution reservoir, containing rinse solution, mounted onboard the support equipment pack. A rinse solution tube is provided for transferring the rinse solution from the reservoir to the sampling tool. The rinse solution is to spray a sampling surface during sample collection. This configuration of the device includes a rinse solution flow control valve and a rinse solution pump for pumping liquid solution to the sampling tool. This liquid solution pump can take any number of forms, such as a centrifugal or peristaltic pump, but a rinse solution pump that has been found to be convenient takes the form of a pressurized container that contains pressurized air and rinse solution. The pressurized air forces a rinse solution out of the rinse solution tube for transfer to the sampling unit. At the sample tube, one or more spray heads are available to spray the rinse solution onto the sampling surface.

Especially when working with a rinse solution, it may be desirable to include a liquid trap connected between the collection unit and the air pump. This would serve as a backup system to prevent any liquid from entering the air pump. A simple ball valve device provides a trap which can be utilized both to prevent the passage of contaminated rinse material from the sampling area back up toward the air pump, as well as controlling the flow of clean rinse material from the rinse material reservoir.

A first ball is held in leak proof engagement against a sealing mechanism by a spring. In a preferred embodiment, the sealing mechanism is an O-ring held in place against a sealing seat. This spring provides sufficient force so as to maintain force to push the ball against the sealing ring. This first ball blocks the flow of material through a flow chamber defined by the sealing seat. This prevents both back flow of contaminated materials toward the air pump, as well as controls the flow of clean rinse solution toward the sampling area.

To obtain a desired amount of fluid flow through the device, a third ball, which extends upward from an inlet tube running between the collection unit and the air pump, is depressed. This third ball is positioned proximate to a second ball, which is positioned in contact with first ball. A flexible impermeable material, such as a latex covering, which prevents contamination from entering into the valve, covers the third ball. By depressing the third ball from its elevated position with regard to the second ball, the second ball is pushed back generally linearly towards the first ball. The first ball is then pushed back against the spring with sufficient force so as to overcome the spring's compressive force against the sealing mechanism and the connection between the sealing sent and the first ball is released. This results in the flow chamber opening and flow of clean rinse material there through permitted.

When pressure to the third ball is released, the spring pushes the first ball back into leak proof engagement against the sealing mechanism. The second ball is also pushed against the third ball. The third ball is then pushed upward into its elevated position with regard to the first and second balls. This provides a leak proof liquid trap that prevents unwanted backflow of material out of the device, as well as unwanted flow of material from the rinse source into the sampling area.

The sample collection portion of the invention is a handheld sampling tool, which is configured to suspend particulate matter in either a wet or dry solution and then to evacuate these suspensions into a collection chamber for later analysis. The handheld sampling tool is comprised of an inlet tube configured to deliver a quantity of a desired solution forming substance into a sampling area and an evacuation tube operatively connected to a source of vacuum pressure to evacuate material from the sampling area to a collection chamber.

The inlet tube can be configured to provide either wet or dry material. In an embodiment utilizing a dry material such as testing the contents of a postal envelope, the inlet tube serves as a gas replacement tube or vent to prevent the envelope being sampled from collapsing when the vacuum force from the evacuation tube is applied. In this embodiment, the inlet tube is a gas replacement tube configured to provide a source of a gas into a sampling environment and to replace an amount of gas being removed from said environment by said evacuation tube. The inlet tube has a first end and a second end. The first end configured for placement within an environment to be sampled, while the second end is connected to a filter configured to prevent passage of contaminants into said inlet tube. Depending upon the types of organisms sought to be recovered, the filter on the end of the inlet tube may be varied or even removed. The inlet tube and the evacuation tube are parallely connected in a position whereby the first end of the inlet tube extends beyond a first end of the evacuation tube so as to create a flow of gas from the inlet tube back towards the evacuation tube. This provides a turbulent flow that is especially effective at disturbing particulate matter which may have settled into a corner, crevice or other portion of the area being tested.

The flow of air or other gas into the area being tested causes the particulate matter in the area to be suspended within the gas and to then be evacuated from the sampling area by the vacuum pump through the evacuation tube.

In an embodiment utilizing a liquid solution or a wet environment, the inlet tube is a conduit for bringing a rinse solution from a rinse tank or other reservoir into the sampling area. The inlet tube has a first end and a second end, the first end configured for placement within an environment to be sampled, and said second end connected to a source of rinse solution. The inlet tube and the evacuation tube are parallely connected in a position whereby the first end of the evacuation tube extends beyond a first end of the inlet tube so as to create a flow of liquid from the inlet tube out towards the evacuation tube. This provides a turbulent flow that is especially effective at disturbing particulate matter that may have settled into a corner, crevice or other portion of the area being tested.

The flow of liquid into the area being tested causes the particulate matter in the area to be suspended within the solution and to then be evacuated from the sampling area by the vacuum pump through the evacuation tube.

In another embodiment utilizing a liquid or wet solution recovery, the tool is specifically adapted to dislodge and suspend materials that are contained within a defined area. In this embodiment, the inlet and the outlet tubes are connected to a head, which is configured to contain, suspend, and evacuate material from a sampling area. In this embodiment, the head has an inlet that connects to the inlet line and an outlet that connects to the evacuation tube. The inlet tube is connected to a nozzle that disperses rinse material in a desired pattern within an area of the head defined by a first spray skirt. This first spray skirt has a plurality of apertures configured to allow passage of air there through, and to allow the passage of liquid out of the area defined by the first spray skirt. A second spray skirt has a circumference greater than the circumference of the first spray skirt and that circumvolves the first spray skirt. This second spray skirt also has a plurality of apertures and is configured to allow passage of air there through. The skirt is shaped and configured to prevent the passage of liquid out of the sampling area defined by the spray skirts. These apertures allow for airflow within the sampling area, and increase the turbulence within this sampling area.

In use, the sampling heads can be placed over an area to be sampled as the liquid flows unto the area being sampled the particulate matter on the surface is suspended within a solution defined by the spray skirts. These spray skirts then contain the liquid material, which is then evacuated into the collection chambers.

Depending upon the individual item being tested, the actual shape and configuration of the spray skirts and the heads can be varied. In one particular embodiment, a generally circular shaped head having a inversely frustoconically shaped skirts is particularly effective in sampling spherically shaped items such as fresh fruit or other similarly shaped items. The shape and configuration of the skirts contain the solution within the sampling area and allow for increased recovery of desired items from these surfaces. Depending upon specific characteristics of the area being sampled, the size, shape, and dimensions of the sampling head can be varied. For example, in other operations where a generally smooth area is to be tested, a square or rectangular shaped sampling head may be more sufficient to meet the needs of the user.

The collection unit may optionally include a pre-filter, which is mounted near the inlet of the collection unit. The pre-filter is to capture particles larger than the containment of interest, such as to separate dirt particles from microbes being collected. The choice of filter size and the use of a filter at all would depend on the contaminant of interest and the matrix in which it is suspended. The pre-filter would typically be a hydrophilic fibrous type filter with a pore size selected for the particular application.

The present invention solves these needs by providing a liquid surface rinse to suspend and aid in detaching microbes. This provides a higher microbial recovery of diverse sampling surfaces. The present invention is efficient and non-destructive of the substrate, and versatile in that it can be used on many surface types and in various positions. It also has improved bacterial containment capabilities for storage or transportation of the collected sample. It also provides for concentration of the microbes for improved detection and may be integrated with diverse bacterial detection systems. In addition, the present invention improves food safety monitoring industry wide, as well as decreasing cross-contamination of multiple sample sites.

One version of the present invention is a handheld wet-vacuum sampling device that allows more efficient collection of liquid or subsequent concentration of microbes onto a removable filter. Aliquots of liquid may be plated or the filter can be easily accessed and cultured directly on various culture media. The concentrated sample can undergo further processing for rapid detection method application directly on the filter with Solid Phase Cytometry or ELISA procedures. Concentrated microbes can also be re-suspended off the filter for PCR or similar procedures.

In another version of the present invention, the present invention first applies a sterile surface rinse solution (SRS) to an item, such as a meat carcass, so as to detach and suspend the microbes. Then, the present invention collects the SRS and suspended microbes through the use of vacuum pressure. The STS first passes through the pre-filter chamber to filter out large debris. Then, the SRS is captured in the liquid collection chamber and contained for transport and/or processing. Once the majority of the SRS and microbes are collected, the filter with the suspended microbes is left on the collection unit with the microbes suspended in a low volume liquid. The microbes may be concentrated onto a 0.2–0.45 μm membrane. However, the filter containing the recovered and concentrated microbes can be disengaged from the present invention.

Depending on whether the filter remains on the collection unit or is removed, the following steps may occur. The suspended microbes from the liquid contaminant unit can be pipetted. Alternatively, the attached filter can be back flushed so that the microbes filter into a conical test tube. Alternatively, the filter can be removed from the unit and can 1) be cultured using conventional methods; 2) have direct ATP or immunoassay detection on the filter; or 3) solid phase cytometry can be performed.

Potential uses for the present invention are numerous. It can be used for pathogenic or routine bacterial monitoring of product and processes in meat and other food production and processing facilities such as meat slaughter, carcasses, and equipment; public health inspected food preparation and sales; restaurants, schools and other public food services; and seafood and aquaculture production, processing, and distribution. The system of the present invention can also be used for air sampling such as for clean room air and equipment; aerosol particles; inorganic particles, dust, radioactive particles, plastics, chemical warfare agents, and asbestos; carbon particles, coal dust or fly ash; and circuit boards and liquid sensitive equipment.

The present invention can be used during biological warfare/terrorism in that it can assist military, civilian, and public health inspectors during monitoring for microbes and chemicals in times of threat or attack by terrorists or hostile forces. One embodiment of the invention includes a dry particle collection sampling tool. This dry embodiment of the present invention allows the inspectors to sample suspicious envelopes and closed boxes through small openings without invading the privacy of the contents.

The present invention can also be utilized during space exploration, such as for food pathogen safety monitoring; bacteria, yeast, and mold growth evaluations of the International Space Station and Bio-Plex. The present invention can also be utilized for biofilm monitoring such as for food production pipelines and storage bins; water processing, heating and cooling distribution lines, or storage equipment; and swimming pools, hot tubs, and related equipment. It can also be used for odor control and gaseous monitoring such as in chemical production and processing industries; and confined livestock production and processing. However, it should be distinctly understood that by no means is this a complete description of the uses of the present invention and it is not intended to limit the scope and use of the present invention, but rather should be seen as illustrative in nature.

Further, the purpose of the foregoing abstract is to enable the United States Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measure by the claims, nor is it intended to be limiting as to the scope of the invention in any way.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1A:
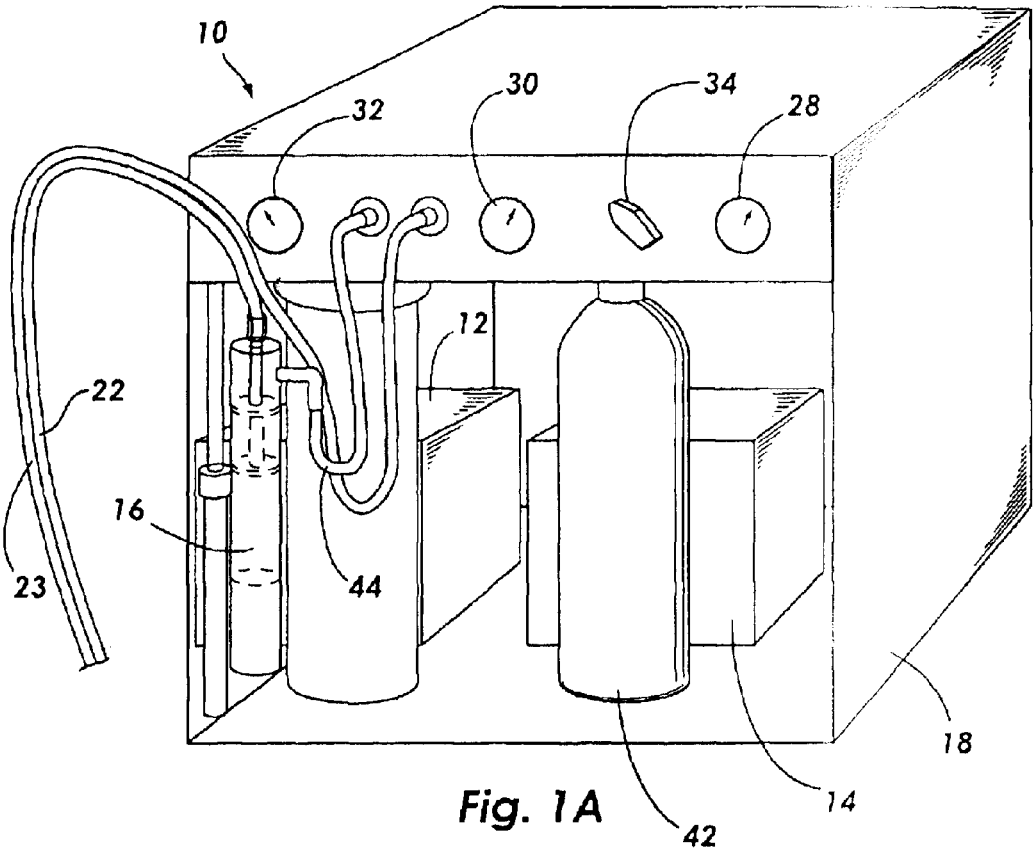
FIG. 1 is a perspective view of the system of the invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Figure 1B:
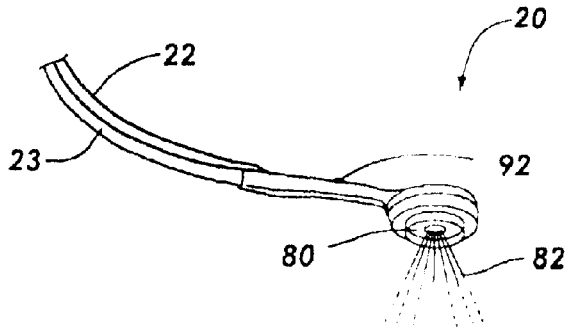
Figure 1C:
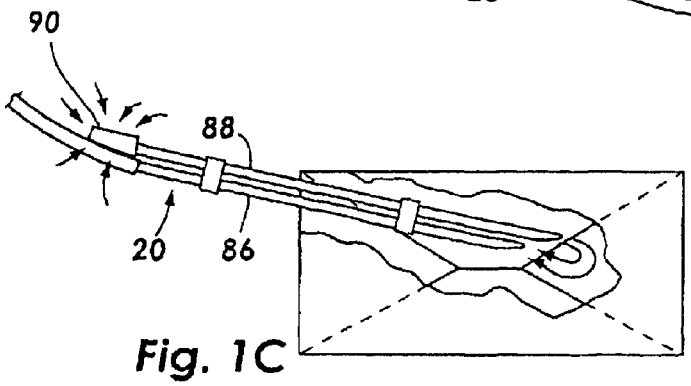

Certain preferred embodiments of the invention are shown in the enclosed drawings, FIGS. 1–11. FIG. 1 is a perspective view of the portable contamination samping system 10. It includes air pump 12, power source 14, collection unit 16, support equipment rack 18, sampling tool 20, samping tool tube 22, and rinse solution pump 40. It also includes pressure gauge 28, which shows the pressure inside the rinse solution reservoir 42, on/off switch 34, which activates the rinse solution system, gauge 30, which shows the pressure of rinse solution in the sample tool tube, and pressure gauge 32, which shows the vacuum pressure in the air line 44. FIG. 1 shows sampling tool 20, which is spraying out rinse solution 82 from a spray nozzle 80 located on the underside of the sampling tool 20.

Figure 2:
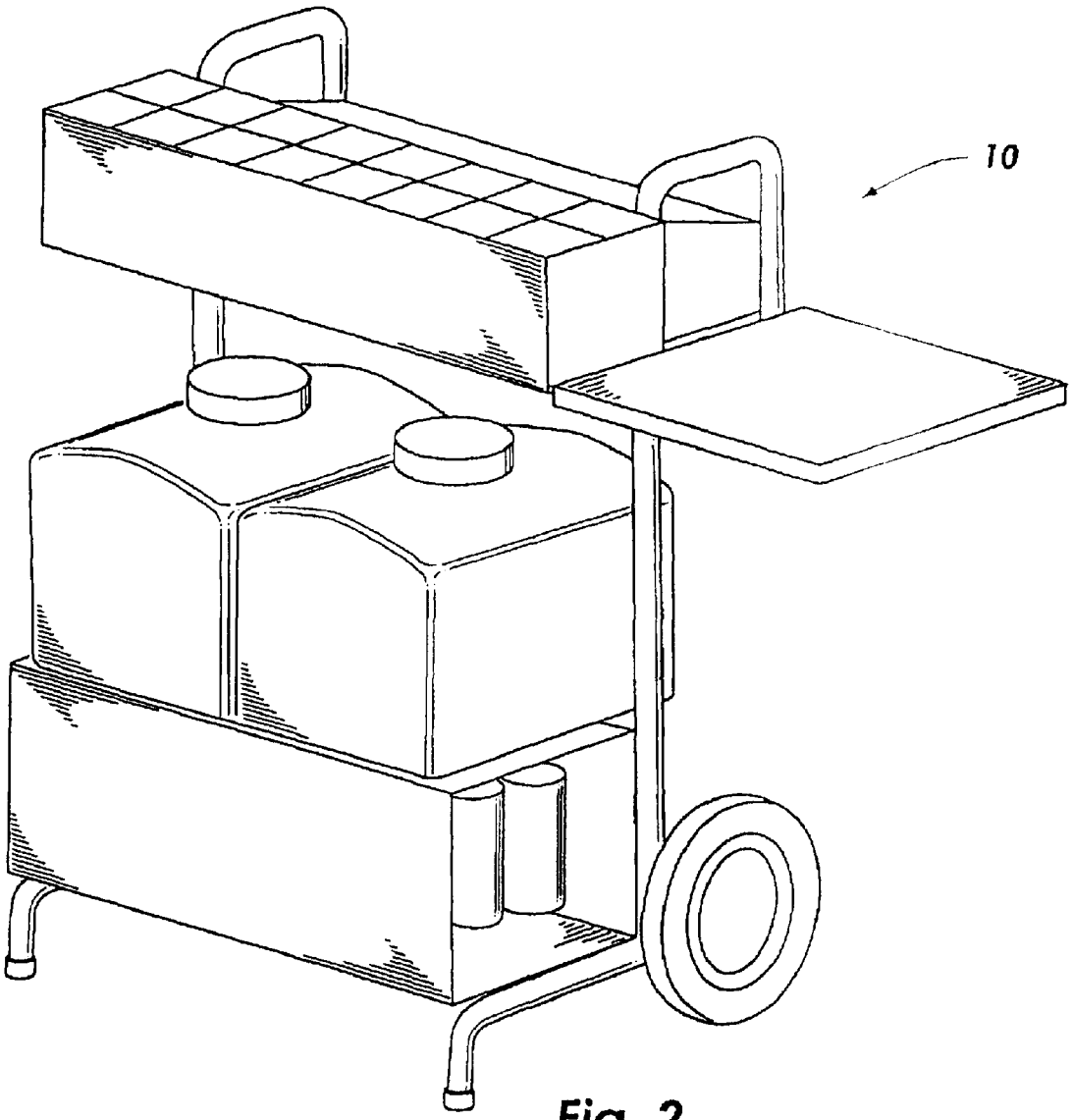
FIG. 2 is a perspective view of a cart based version of the invention.

FIG. 2 shows the portable containment sampling system 10 of the invention configured in a cart format. All of the same components of the system of FIG. 1 would be present in such a cart.

Figure 3:
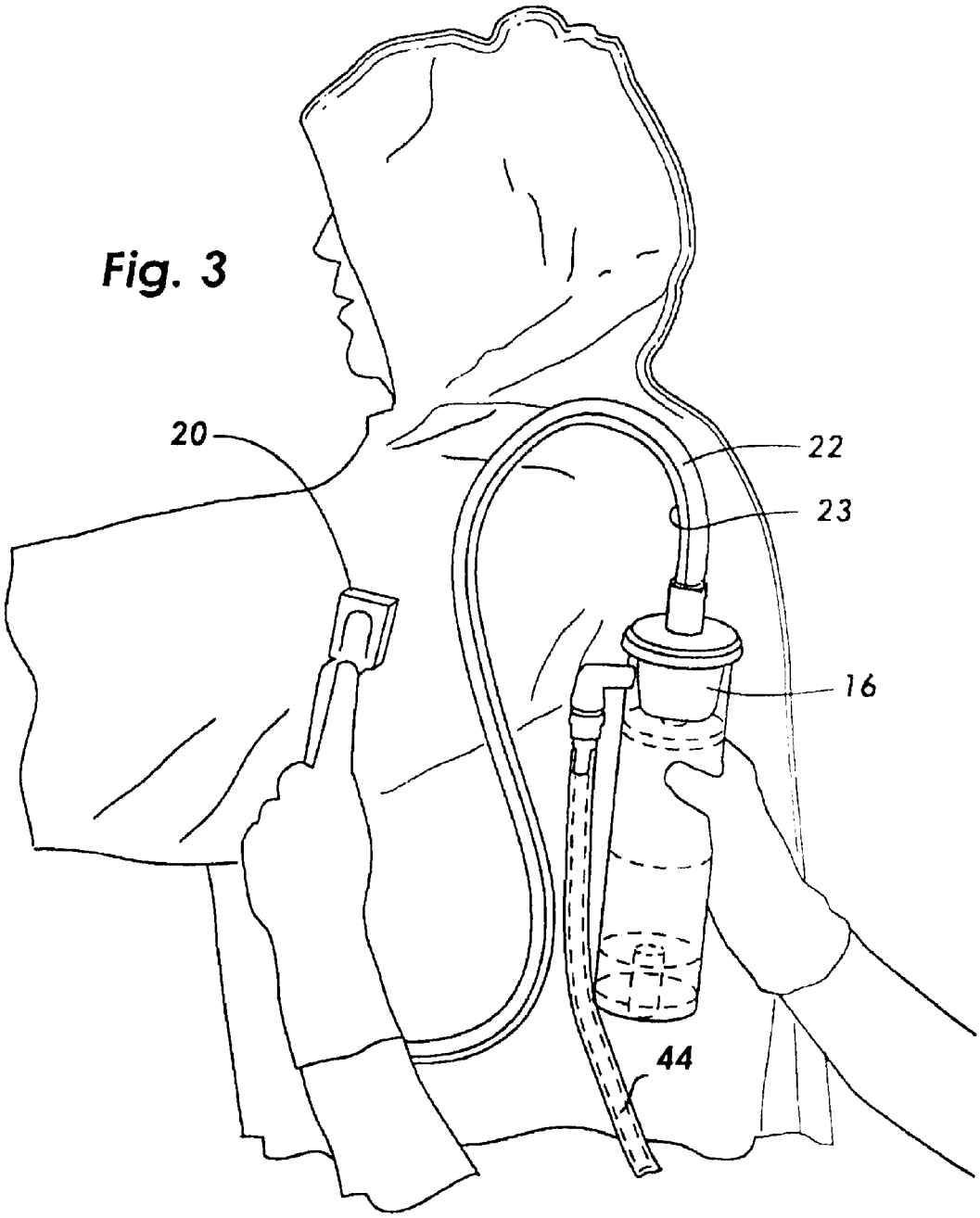
FIG. 3 shows the system of the invention being used to test for contamination of a person.

FIG. 3 shows the system of the invention being used to test for contamination in the field. Shown is collection unit 16, which includes vacuum line 44, sample tool tube 22, and sampling tool 20. In this configuration, the vacuum line 44 and the sample tool tube 22 are joined together as a single, double tube. The vacuum line 44 continues from the collection unit 16 to the vacuum pump (not shown). In this configuration, liquid from the sample tool tube 22 is sprayed through the sampling tool 20 onto the surface being sampled. In this case, that surface is the clothing of a person. Immediately after the rinse solution is sprayed onto the clothing, it is drawn back into the sampling tool 20 by airflow, and returns to the collection unit 16 by way of the vacuum line 44. In this configuration of the collection unit 16, the rinse solution is retained in the collection unit 16 by means of a hydrophobic filter 24.

Figure 4:
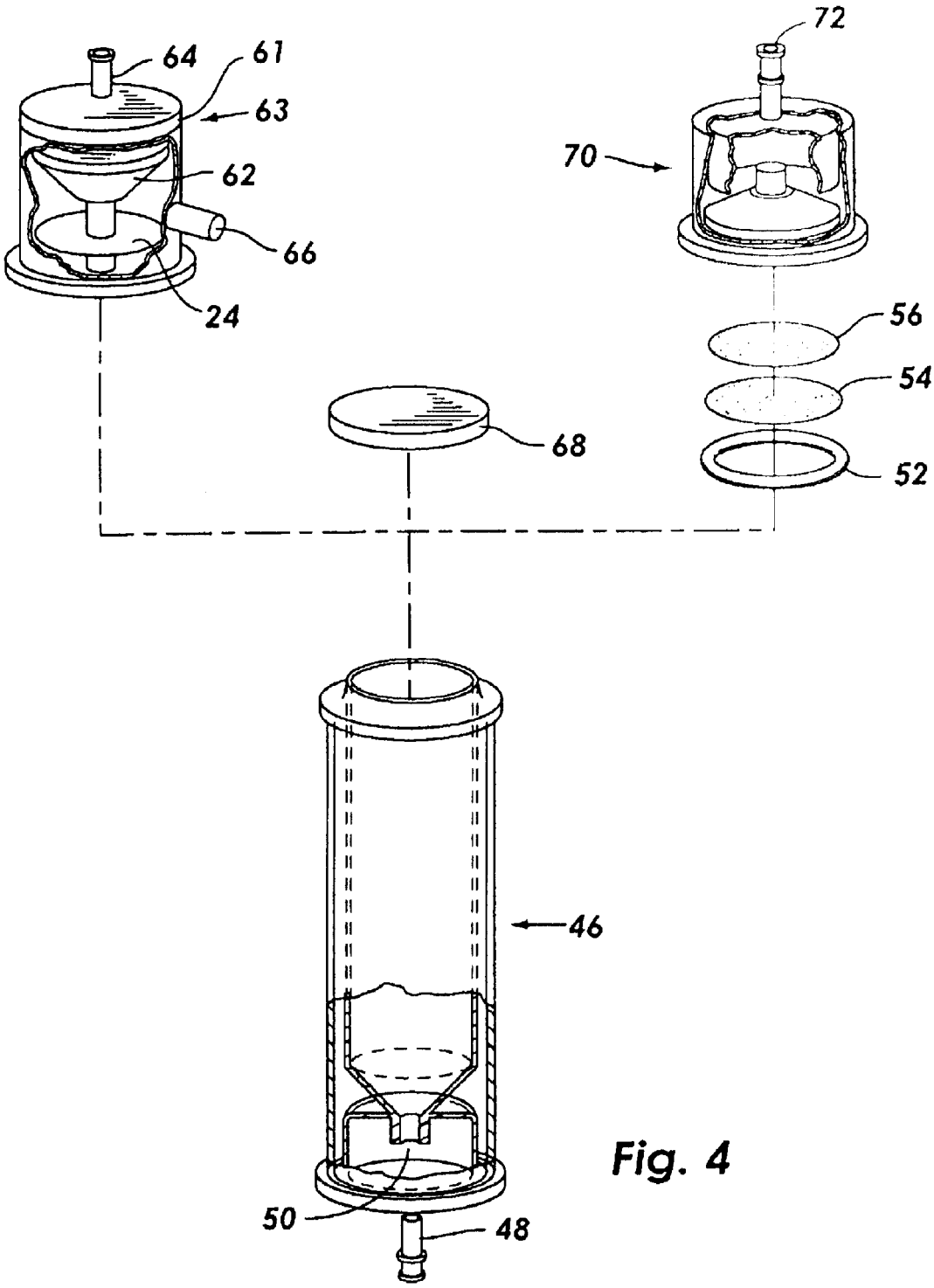
FIG. 4 is an exploded view of a collection unit of the invention.

FIG. 4 is an exploded view of a collection unit of the invention. It includes fluid chamber 46, which may be tapered at one end, and which includes airlock 48. Airlock 48 seals drain orifice 50 in the collection unit 16. The collection unit 16 also includes O-ring 52, filter 54, and filter support 56. When assembled in the field, the fluid chamber 46 would be used in conjunction with cap 58. The cap 58 includes hydrophobic filter 24, and may optionally include pre-filter 60, which removes large particles from the sample and holds them for rinsing by rinse solution. Below the pre-filter 60 is funnel 62, which directs rinse solution and contaminants through the hydrophobic filter and into the fluid chamber 46. The cap 58 includes inlet 64 and outlet 66. The inlet 64 is connected to the collection head 20 shown in FIGS. 1 and 3. The outlet is connected to the air pump 12 as shown in FIG. 1. As the sample is taken, the sample and the media in which it is contained, whether air or liquid, passes through the pre-filter (optional) through the hydrophobic filter 24 by way of the funnel 62 and into the fluid chamber 46.

When sampling is done, the cap 58 can be removed and replaced with a seal 68, which hermetically seals the sample in the fluid chamber for storage, for instance in a refrigerated or cooled chamber, and transport. The seal 68 can be attached to the fluid chamber 46 by a number of means including a clamp that joins corresponding ridges on the fluid chamber and the seal 68 together. Also provided with this embodiment of the collection unit 16 is filter head 70. In the lab, the seal 68 would be removed and the filter head 70 would be attached. At that point, the fluid chamber 46 would be inverted, so that the sample in the fluid would be located above the filter head 70. At that time, the fluid in the fluid chamber 46 would be drawn through the hydrophilic filter 54, and through the filter support 56, and out the second drain 72. At that point, the hydrophilic filter 54 could be removed from the unit, and incubated to be used to provide testing material to test for the presence of the contaminant of interest, such as microorganism, chemicals, or radioactivity.

Figure 5:
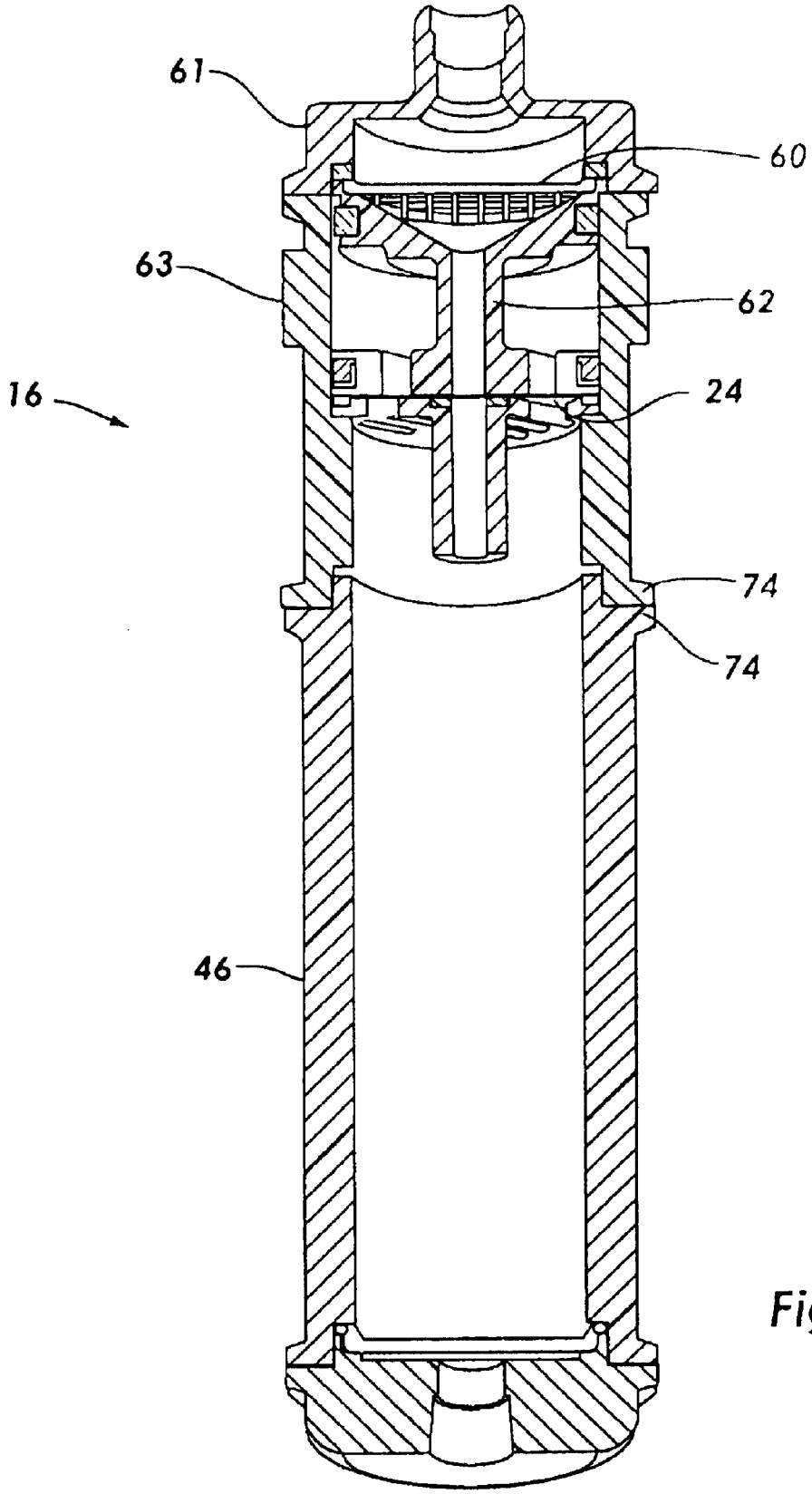
FIG. 5 shows an alternative collection unit which may be utilized with the system of the invention.

FIG. 5 shows an alternative collection unit 16 which may be utilized with the system of the invention. It includes pre-filter 60, funnel 62, and hydrophobic filter 24. This version of the device also includes a fluid chamber 46. This unit of the device has ridges 74 between each of the various sections of the collection unit 16. These sections are held together by a clamp that encircles and covers the ridges 74 and clamps the unit together. Other devices for clamping the units together are also possible, such as a friction fit with O-rings, twist and lock connections, and connections using other types of clamps. The collection unit shown in FIG. 5 would be utilized in a similar manner as that previously described in FIG. 4.

Figure 6:
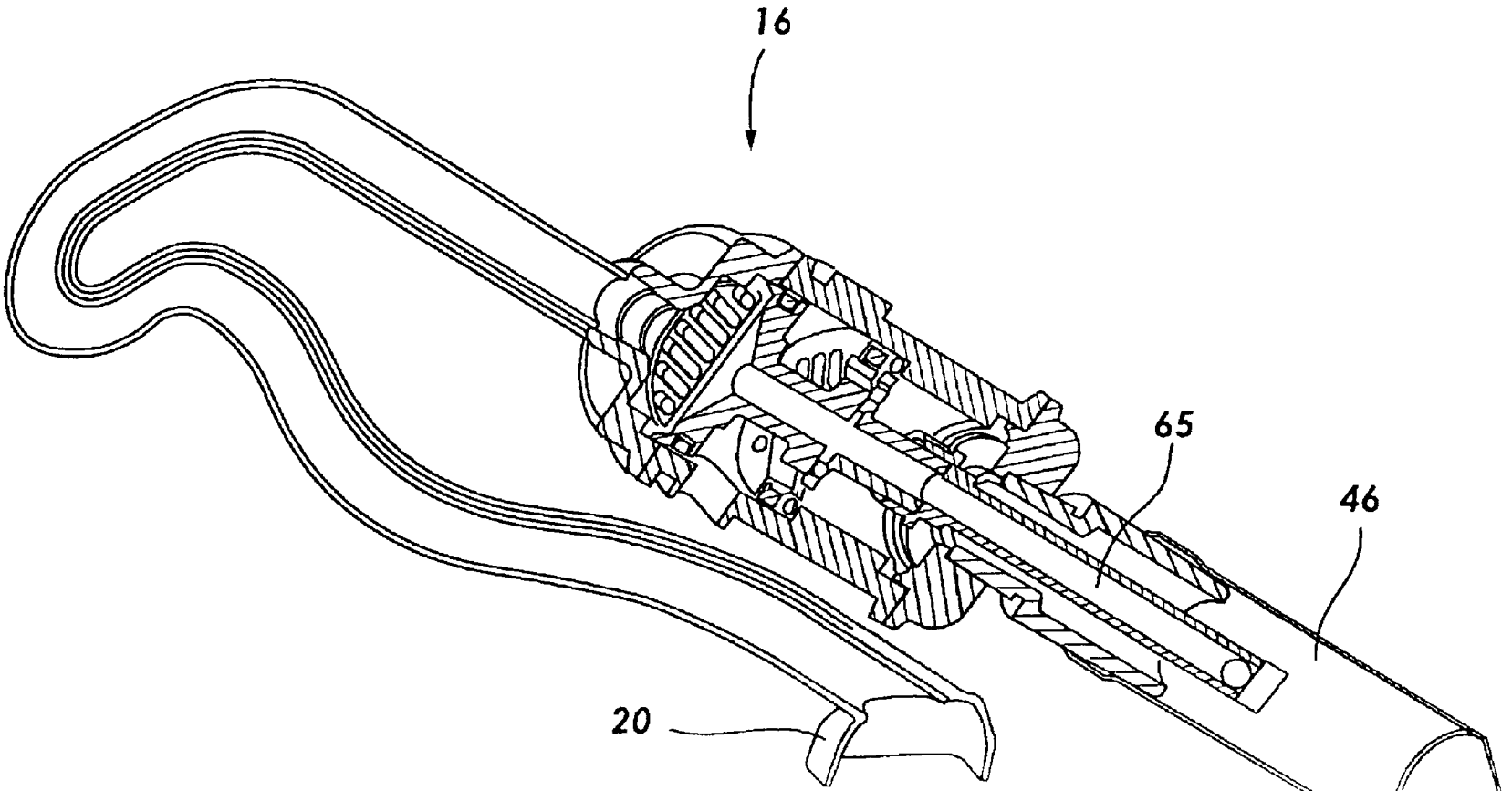
FIG. 6 shows another configuration of a collection unit with an attached sampling tool.

FIG. 6 shows another configuration of a collection unit 16, with an attached sampling tool 20. In this configuration of the device, the fluid chamber 46 takes the form of a cylindrical tube with a tapered bottom. This is similar to a test tube, and would be treated like a test tube on the unit. When filled with the appropriate amount of rinsing solution and sample, the fluid chamber 46 would be removed, capped, and sent off for analysis at another site. The sampling tool 20 shown in FIG. 6 is shown in greater detail in FIG. 7.

Figure 7:
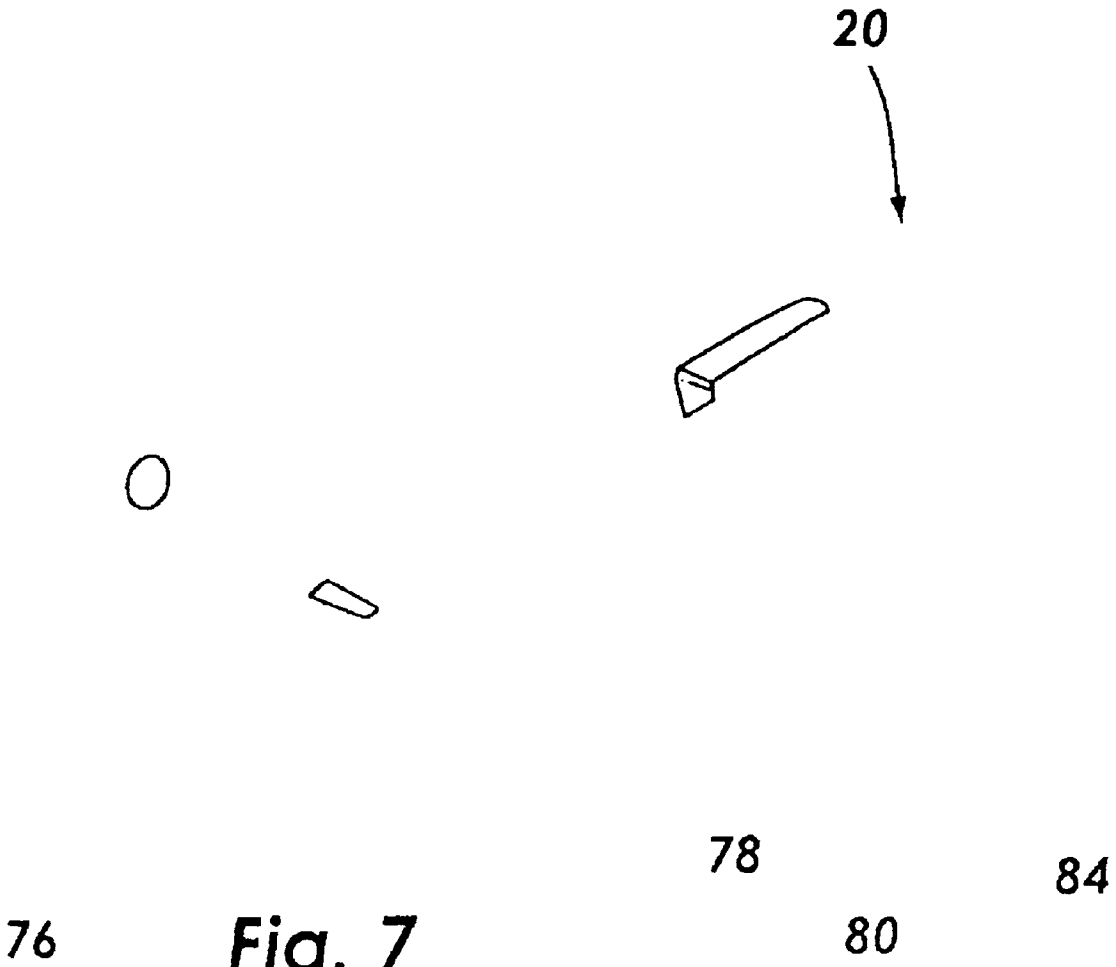
FIG. 7 shows a sampling tool with a flow switch that turns on or off the flow of rinsing solution.

FIG. 7 shows a sampling tool 20 with a flow switch 76, which turns on or off the flow of rinsing solution. The sampling tool 20 of FIG. 7 includes an outer skirt 78. The outer skirt 78 serves to contain the rinse solution that is sprayed out of the spray nozzle 80. The outer skirt is preferably made of a flexible material, and acts like a squeegee. It also has small vents or notches along its periphery, which allows air to enter, and by forcing the air into a narrow channel, causes the air speed of the entering air to be very fast. This results in improved pickup of the rinse solution and the contaminants.

Figure 8:
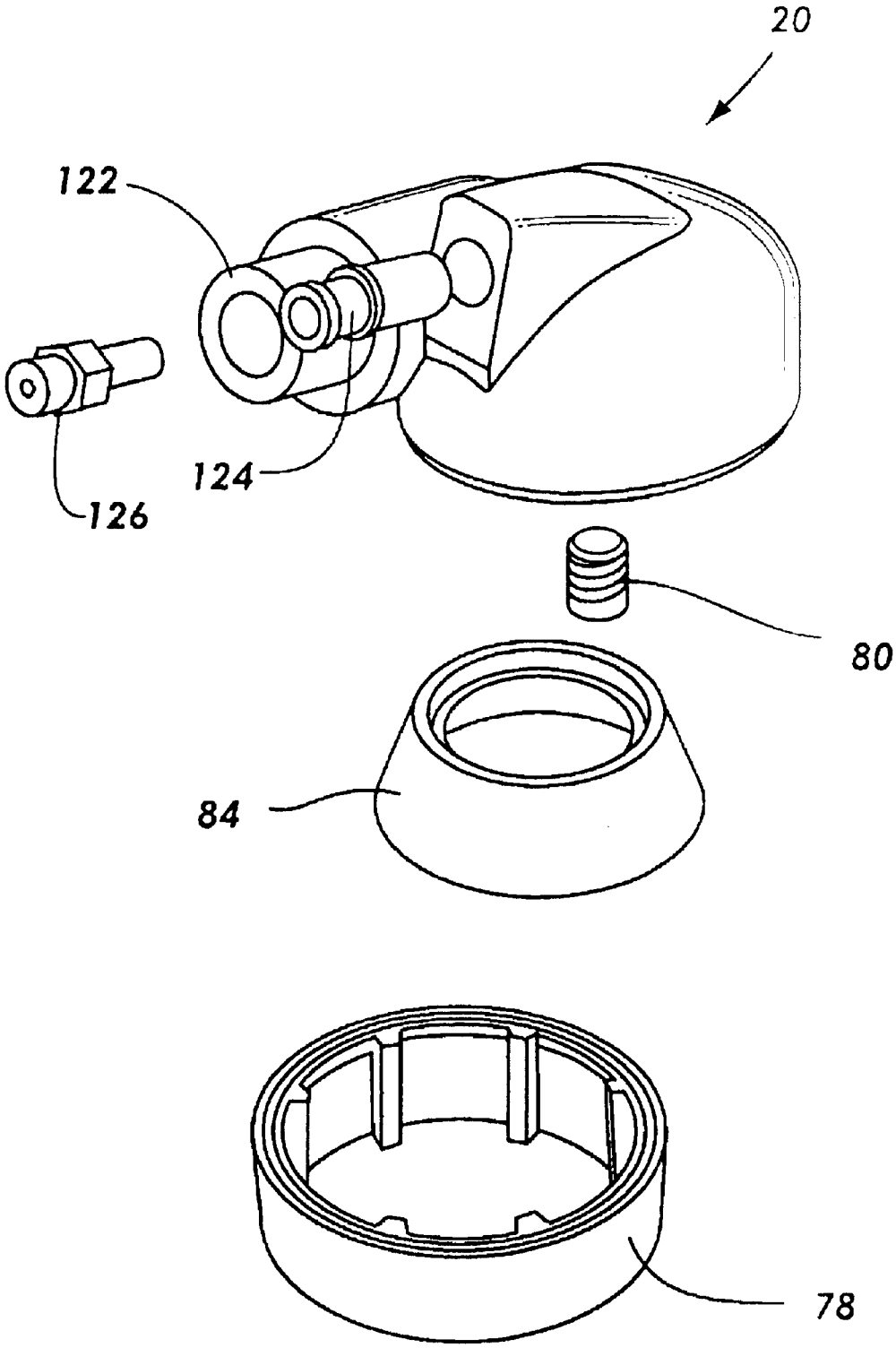
FIG. 8 shows an exploded perspective view of another embodiment of a sampling tool.

FIG. 8 shows an exploded perspective view of another embodiment of a sampling tool. This version of the sampling head is similar to the version shown in FIG. 7, but in addition to the outer skirt 78, also includes an inner skirt 84. The two skirts acting together serve as a better seal and thus prevent a rinse solution from escaping the sampling head 20. They also help to channel and direct the airflow so that there is high speed air passing over the sampling surface at the edges of the outer skirt 78 and the inner skirt 84. Also shown is the spray nozzle 80.

Figure 9:
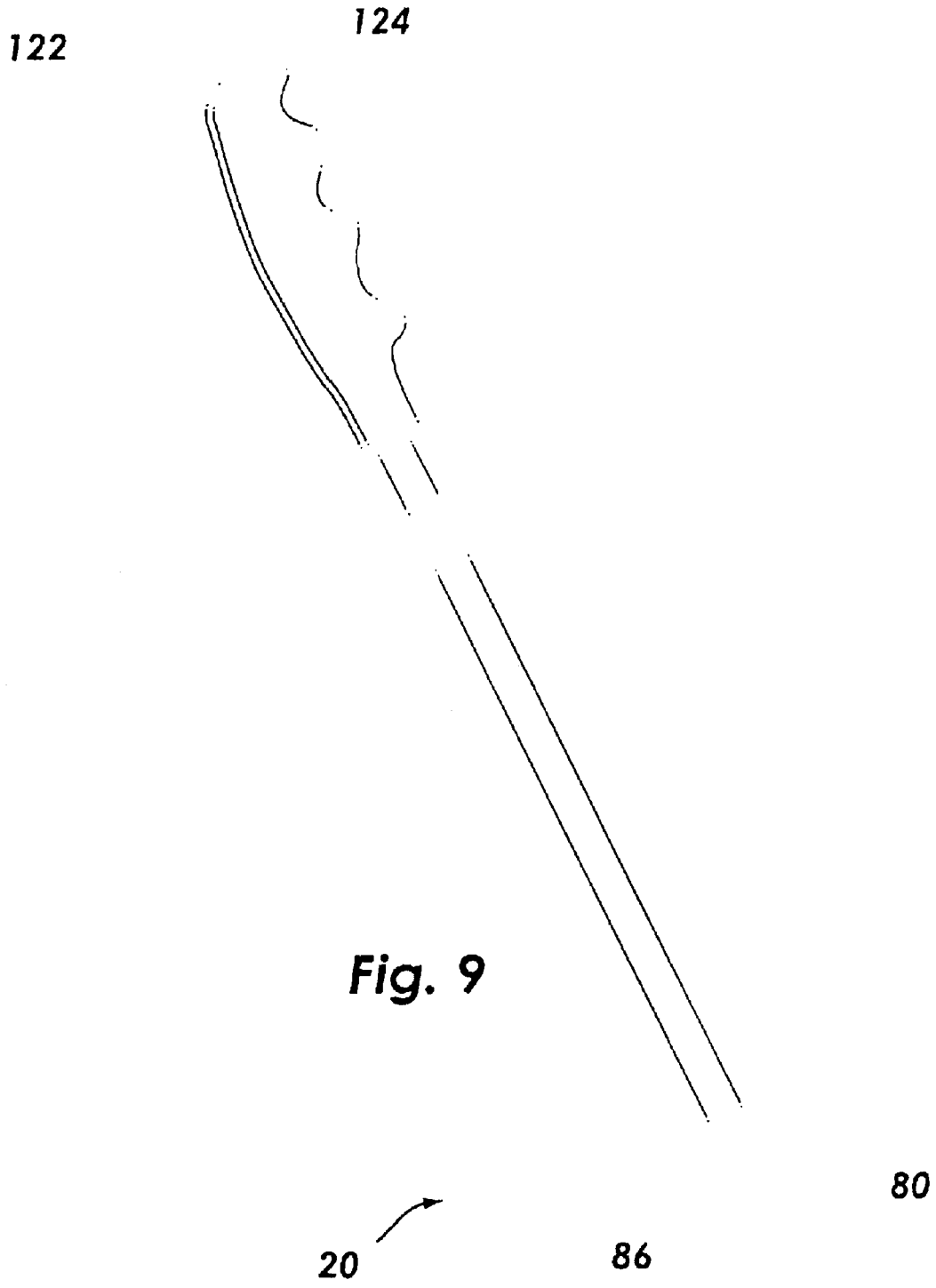
FIG. 9 shows another version of a sampling tool.

FIG. 9 shows another version of a sampling tool 20. It includes a collection tube 86 and a spray nozzle 80, which takes the form of a tube parallel to the collection tube. Rinse solution 82 is pumped through the spray nozzle 80 and is used to dislodge or solubilize sample material. The rinse solution and the suspended sample material is collected in the collection tube 86 and returned to the collection unit 16 (not shown in FIG. 9).

An additional embodiment of sample head 20 is shown in FIG. 1. This embodiment includes a collection tube 86 to which is attached a vent tube 88. This embodiment of a sampling tool is designed to be inserted into a closed structure such as an envelope, so that the contents of the envelope can be sampled. This allows the privacy of the envelope to be maintained by cutting a small hole into a corner of the envelope and inserting the sample tool shown in FIG. 1. As air is pulled out through the collection tubing 6, air from the outside is allowed to enter the vent tube 88. Thus the bag or envelope does not collapse. Air entering the vent tube 88 also provides some turbulence so that particulate matter can be scrubbed off the container wall and collected in the collection tube 86. An air filter 90 is provided so that air entering the envelope or other structure is guaranteed not to contaminate the envelope. Structures into which this could be inserted include envelopes, boxes, storage containers, shipping containers, and any sort of closed structure.

Figure 10:
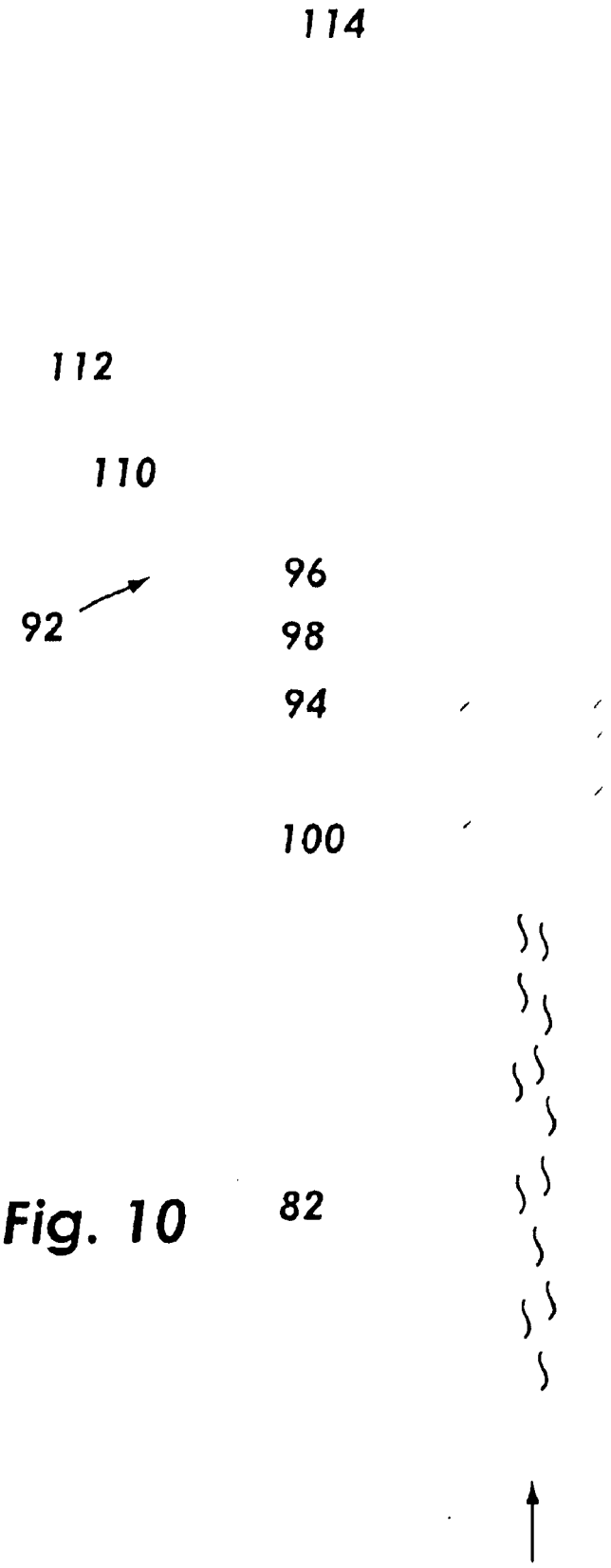
FIG. 10 shows a valve of the invention.

FIG. 10 shows a valve of the invention. This valve is utilized in a sampling tool 20, and is shown in FIG. 1 as valve 92. As shown in FIG. 10, valve 92 is comprised of a first ball 94, a ball seat 96, and an o-ring 98. It also includes a spring 100, a second ball 110, and a third ball 112. Rinse solution 82 is present in the sample tool tube 22. Spring 100 presses the first ball 94 into the o-ring 98, thus sealing the sample tool tube from passage of the rinse solution 82. The first ball 94 is moved away from the o-ring 98 when the user presses on the latex boot 114 and depresses the third ball 112, and the second ball 110. While the third ball 112 is depressed, rinse solution 82 flows through the sample tool tube 22.

Figure 11:
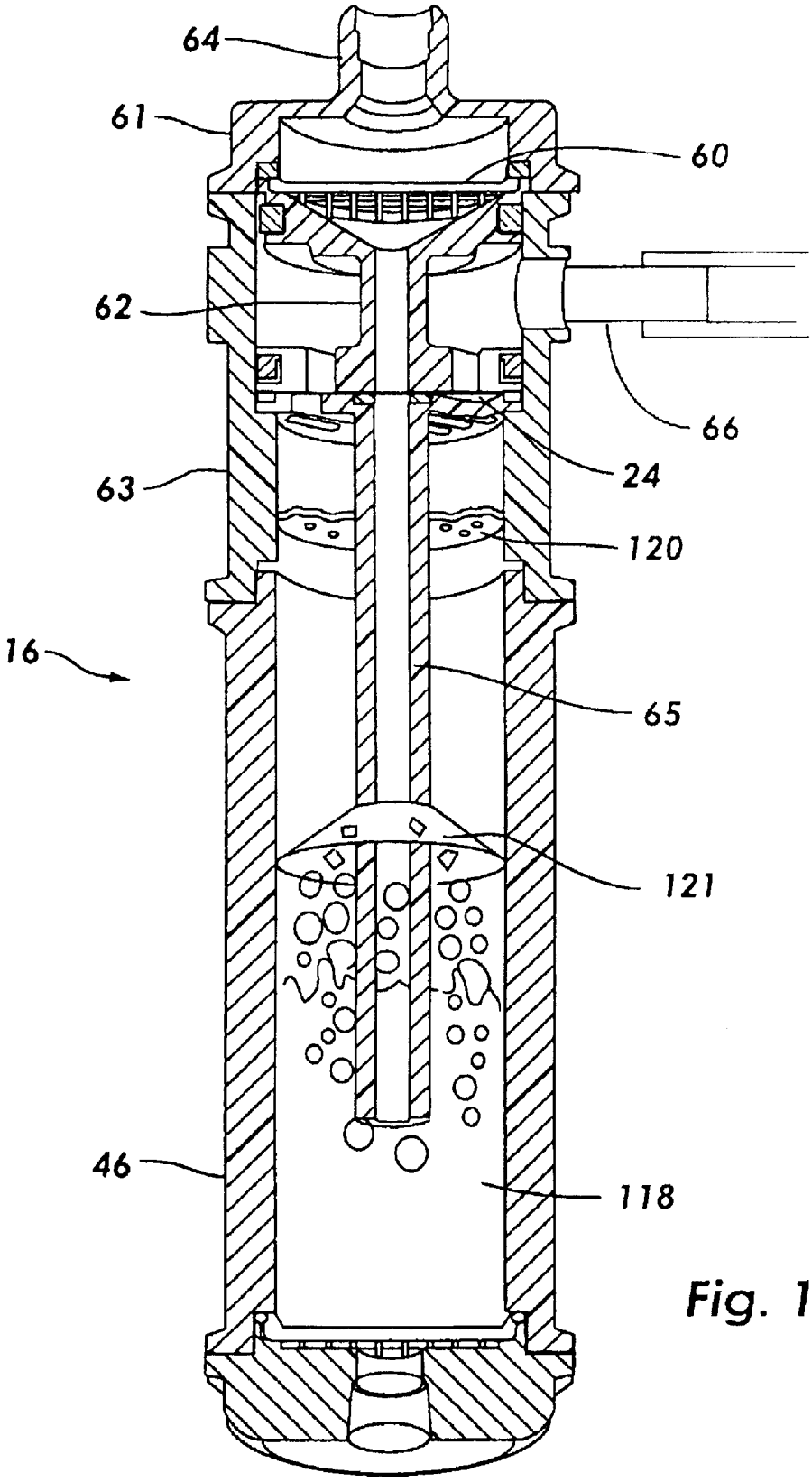
FIG. 11 shows another preferred embodiment of the invention.

FIG. 11 shows another preferred embodiment of the invention. This embodiment is configured for sampling a gas, and includes an elongated tube 116. Catchment fluid 118 is contained in the fluid chamber 46. The elongated tube 116 extends into the catchment fluid 118. When air is evacuated by the air pump through the outlet 66, air to be sampled is drawn into the inlet 64. From the inlet 64, gases to be sampled pass through an optional prefilter 60, and through a funnel 62. The air is then released below the surface of the catchment fluid 118, and is drawn through a hydrophobic filter 24 and out the outlet 66. A baffle disk 120 is present which blocks bubbles from bursting and propelling droplets of fluid onto the upper side walls of the fluid chamber 46. The baffle disk 20 may be a flat disk or frustoconical shaped as shown in FIG. 11. Either configuration of baffle disk 120 is preferably configured to be able to freely move up and down the elongated tube 116. This causes a washing and cleaning of the side walls of the fluid chamber 46. This is desirable because microbes may be in liquid droplets which adhere to the side walls of the fluid chamber 46. If left for very long on the side wall, the droplet of catchment fluid would dry out, and the microbe could be killed. The washing action of the baffle disk helps to recover such microbes, and greatly reduces the amount of droplets which are spattered on the side walls of the fluid chamber 46.

The present invention was used in comparison with existing meat testing methods, including sponge (SP) and excision (EX) techniques. Hog and beef carcass tissue samples were spiked with variable levels of beef fecal slurry E. coli (85 to 715 cfu's per 100 $cm^2$) and sampled at 24 hours (3° C., 95% humidity). E coli recovery off adjacent tissue areas were measured using conventional culture methods (pour plates, M-endo media) on excision (EX) and sponge (SP) solutions (0.1% peptone) following two minutes on a stomacher in whirl-pac filter bags (Nasco). The present invention protocol included 50–75 milliliters surface rinse solution applied under low pressure within the sampling head during two passes over the 100 $cm^2$ tissue area. The present invention filters were removed and cultured directly on prepoured "M-endo" plates.

The results demonstrate that the pooled recovery rates of the present invention and EX were similar. The present invention recovered 45% in hogs and 52% in beef, while EX recovered 42% in hogs and 54% in beef, whereas the SP recovered 30% on hogs and 16% on beef (n=19–33 per tissue per method). Sponge sampled areas were subsequently resampled utilized the present invention and/or EX methods. E. coli recovery from resampled tissue using either method was slightly lower for the present invention (17%) compared to EX (21%) following sponging. Excision recovered an additional 12% E. coli following the present invention's sampling and 10% more following SP and the present invention collection. Summed recoveries of SP+EX+the present invention on the same area was similar to recovery using the present invention or EX as the only collection method. Surface distortion and bacterial encapsulation in surface cracks or crevices and lipids may affect repeat sampling results. However, subsequent repeat sampling with either EX or the present invention clearly demonstrated that significant numbers of microbes remain on tissue surfaces following sponge sampling and that either alternative method (EX or the present invention) may be used to recover similar numbers of these bacteria.

This data further demonstrates that significant numbers of bacteria may remain on the meat carcass tissue surfaces following sponge sampling. The data also show that utilization of the present invention system offers a non-destructive sampling method that compares well with excision recovery data and will collect at least twice as many microbes as the sponge off adjacent spiked tissue areas.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

We claim:

1. A handheld sampling tool comprising:

an inlet tube configured to deliver a quantity of rinse solution from a rinse solution source to a surface being sampled, said inlet tube having a valve configured to control flow of a liquid through said inlet tube, said inlet tube connected to a sampling head configured to disperse said rinse solution through a nozzle over a sampling surface;

an evacuation tube configured to connect with a source of vacuum pressure to evacuate said rinse solution from said sampling surface, said evacuation tube connected to an outlet of said sampling head, and an outer [flexible] retaining skirt configured to define a sampling chamber and to hold said rinse solution therein, said outer [flexible] retaining skirt defining plurality of air flow apertures configured to provide desired levels of air flow and turbulence within said sampling chamber so as to assist in recovering desired materials from said sampling surface.

2. The handheld sampling tool of claim 1 further comprising:

an inner [flexible] retaining skirt configured to assist said outer [flexible] retaining skirt.

3. The handheld sampling device of claim 2 wherein said first and second retaining skirts are configured to sample a generally spherical surface.

4. The handheld sampling device of claim 3 wherein said valve comprises a first ball and a first ball seat, said ball configured to block flow of a rinse solution through a flow chamber defined within said inlet tube when said ball is seated against said ball seat and to allow passage of liquid through said inlet tube when said first ball is not seated against said ball seat.

5. The handheld sampling tool of claim 4 wherein said valve further comprises a second ball and a third ball, said second ball positioned adjacent said first ball, and said third ball positioned adjacent said second ball, said balls configured so that depressing said third ball displaces said second ball and said first ball allowing flow of rinse solution through said inlet tube.

6. The handheld sampling device of claim 1 wherein said handheld sampling device further comprises a second [flexible] retaining skirt positioned within said sampling chamber.

7. The handheld sampling device of claim 6 wherein said first [flexible] retaining skirt and said second [flexible] retaining skirt are configured to prevent rinse solution from escaping from said sampling chamber, when said sampling device is used upon a sampling surface.

8. The handheld sampling device of claim 7 wherein said first and second retaining skirts are configured to sample a generally spherical surface.

* * * * *